US007052464B2

(12) United States Patent
Wodnicki

(10) Patent No.: US 7,052,464 B2

(45) Date of Patent: May 30, 2006

(54) ALIGNMENT METHOD FOR FABRICATION OF INTEGRATED ULTRASONIC TRANSDUCER ARRAY

(75) Inventor: Robert G. Wodnicki, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 195 days.

(21) Appl. No.: 10/751,290

(22) Filed: Jan. 1, 2004

(65) Prior Publication Data

US 2005/0148132 A1 Jul. 7, 2005

(51) Int. Cl.
*A61B 8/00* (2006.01)

(52) U.S. Cl. ..................................... 600/459; 29/25.35

(58) Field of Classification Search ................ 600/140, 600/170, 180, 437, 459, 460; 367/140, 162, 367/173, 174, 170, 178, 180–182; 29/25.35
See application file for complete search history.

(56) References Cited

U.S. PATENT DOCUMENTS

| | | | | |
|---|---|---|---|---|
| 6,384,516 | B1 | 5/2002 | Fraser | 310/334 |
| 6,571,445 | B1 * | 6/2003 | Ladabaum | 29/25.35 |
| 6,632,178 | B1 * | 10/2003 | Fraser | 600/459 |
| 6,659,954 | B1 * | 12/2003 | Robinson | 600/459 |

* cited by examiner

*Primary Examiner*—David Vu
(74) *Attorney, Agent, or Firm*—Fletcher Yoder

(57) ABSTRACT

An integrated circuit is fabricated by micromachining a hexagonal array of cMUT elements on top of a substrate comprising a hexagonal array of CMOS cells. Each cMUT element overlies a respective CMOS cell in one-to-one correspondence. During layout of the mask for micromachining the cMUT layer, either the hexagonal pattern or the alignment key is rotated until an axis of symmetry of the hexagonal pattern is aligned with an axis of the alignment key. Later, when the mask is superimposed on the CMOS substrate, the alignment key on the mask is aligned with an alignment key on the substrate. This ensures that the cMUT elements formed by optical lithography will be matched to the CMOS cells.

4 Claims, 4 Drawing Sheets

ALIGNMENT METHOD FOR FABRICATION OF INTEGRATED ULTRASONIC TRANSDUCER ARRAY

STATEMENT REGARDING FEDERALLY SPONSORED RESEARCH & DEVELOPMENT

The United States Government may have certain rights in this invention pursuant to U.S. Government Contract Number DAND17-02-1-0181 awarded by The U.S. Army Medical Research Acquisition Activity.

BACKGROUND OF THE INVENTION

This invention generally relates to the fabrication of micromachined ultrasonic transducers. In particular, the invention relates to the fabrication of ultrasonic transducer arrays on CMOS wafers.

Recently semiconductor processes have been used to manufacture ultrasonic transducers of a type known as micromachined ultrasonic transducers (MUTs), which may be of the capacitive (cMUT) or piezoelectric (pMUT) variety. cMUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave.

One advantage of MUTs is that they can be made using semiconductor fabrication processes, such as microfabrication processes grouped under the heading "micromachining". As explained in U.S. Pat. No. 6,359,367:

> Micromachining is the formation of microscopic structures using a combination or subset of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein. The systems resulting from such micromachining processes are typically referred to as "micromachined electromechanical systems" (MEMS).

The cMUTs are usually hexagonal-shaped structures that have a membrane stretched across them. This membrane is held close to the substrate surface by an applied bias voltage. By applying an oscillatory signal to the already biased cMUT, the membrane can be made to vibrate, thus allowing it to radiate acoustical energy. Likewise, when acoustic waves are incident on the membrane the resulting vibrations can be detected as voltage changes on the cMUT. A "cMUT cell" is the term that will be used herein to describe a single one of these hexagonal "drum" structures. The cMUT cells can be very small structures. Typical cell dimension are 25–50 microns from flat edge to flat edge on the hexagon. The dimensions of the cells are in many ways dictated by the designed acoustical response. It may not be possible to create larger cells that still perform well in terms of frequency response and sensitivity desired.

Ultrasonic probes have been designed based on cMUT technology. In one known design, multiple cMUT cells are grouped together and the electrodes of cells in a particular group are hard-wired together to create larger transducer elements. One can form still larger elements, e.g., linear elements, by electrically connecting elements (i.e., so-called "subelements" comprising groups of hard-wired cMUT cells) together using a switching network. The larger elements can be reconfigured by changing the state of the switching network. However, the elements consisting of only one set of CMUT cells all hard-wired together cannot be reconfigured.

In accordance with one proposed architecture, each element comprises a multiplicity of hexagonal MUT cells arranged in a honeycomb pattern with the electrodes on the membranes hard-wired together. The outer ring of MUT cells in each element forms another hexagon. These elements can be reconfigured to form larger elements using a switching network. An array of such smaller elements can be integrated with conventional metal oxide semiconductor (CMOS) switches and preamplifier/buffer circuits onto a silicon wafer to provide reconfigurable beamforming elements. MEMS technology enables the realization of a two-dimensional cMUT array that resides on top of the CMOS electronics.

In accordance with a known method of manufacture, a pre-fabricated CMOS wafer is planarized prior to commencing the cMUT fabrication process. The CMOS wafer comprises an array of cells, each cell being composed of circuit elements that are used to provide required functions to its associated cMUT element locally. Connections between the plane of the CMOS cell matrix and the plane of the cMUT element array can be accomplished vertically.

Lithography is typically used in the fabrication of MEMS devices. The process typically involves the transfer of a pattern to a photosensitive material by exposing selected areas to a source of radiation such as light. The photosensitive material undergoes a change in its physical properties when exposed to radiation. Typically a mask is used that allows light to pass through and impinge only upon selected regions of the photosensitive material. In lithography for micromachining, the photosensitive material is typically a material (i.e., a photoresist) whose chemical resistance to developer solution changes when exposed to radiation of a specific wavelength. The developer solution is used to etch away one of the two regions (exposed or unexposed). A photosensitive layer can be used as a temporary mask when etching an underlying layer, so that the pattern can be transferred to the underlying layer. The photosensitive layer may also be used as a template for patterning deposited material.

In the fabrication of MEMS devices, different layers of the structure being fabricated must be aligned with each other. Each mask should have fiducial, i.e., alignment, marks, which are aligned with corresponding fiducial marks on the previously patterned layers, so that the corresponding layer can be registered with the other layers. The alignment mark on a mask may be transferred to the wafer, allowing an alignment mark on a subsequent mask to be aligned with the alignment mark on the wafer.

Mask making typically comprises layout and pattern transfer to the mask. The term "layout" refers to the process of defining the pattern that will appear on the mask, which in turn defines the geometry of the device being fabricated. Layout is typically performed in a graphical editing tool that manipulates a file containing layers of patterns. Each layer represents a respective mask. The layout tool allows the user to view and edit all of the layers together or selected layers. The pattern defined during layout must then be transferred to an optically opaque mask coating on an optically transparent mask substrate.

To fabricate a cMUT layer on top of a CMOS layer, an appropriate mask must be made using a conventional layout tool. In the case of a honeycomb pattern of hexagonal CMUT elements, there exist three natural axes of symmetry oriented at 60° relative to each other. The natural way to route signal and control lines in this coordinate system is along the axes of symmetry. In a rectilinear array of CMOS devices the natural axes of symmetry are mutually orthogonal. In this case, the natural way to route signal and control lines is along one of the orthogonal axes. While non-orthogonal lines can be drawn in standard CMOS processes, this can increase the incidence of defects and complicates mask production. When integrating cMUT devices that are distributed in a hexagonal or honeycomb grid on top CMOS devices that are distributed in a rectilinear grid, mismatch of unit elements occurs.

There is a need for methods of aligning a hexagonal grid of cMUT elements with a rectilinear grid of CMOS cells during micromachining. In particular, each hexagonal cMUT element must match up with its respective rectangular CMOS cell.

BRIEF DESCRIPTION OF THE INVENTION

The present invention is directed in part to an integrated circuit comprising a micromachined hexagonal array of cMUT elements on top of a substrate comprising a hexagonal array of CMOS cells and in part to methods of aligning the respective arrays so that each cMUT element overlies a respective CMOS cell in one-to-one correspondence. During layout of the mask for micromachining the cMUT layer, either the hexagonal pattern or an alignment key is rotated until an axis of symmetry of the hexagonal pattern is aligned with an axis of the alignment key. Later, when the mask is superimposed on the CMOS substrate, the alignment key on the mask is aligned with an alignment key on the substrate. This ensures that the cMUT elements formed by optical lithography will be matched to the CMOS cells.

One aspect of the invention is an alignment method comprising the following steps: (a) laying out a pattern representing a hexagonal arrangement of cMUT elements having axes of symmetry, the laid-out pattern comprising a first set of graphical data; (b) processing the first set of graphical data to rotate the pattern by a predetermined angle relative to a fixed rectilinear frame of reference having two mutually orthogonal axes, the predetermined angle being selected so that an axis of symmetry of the hexagonal arrangement of hexagonal cMUT elements is aligned with an axis of a first fixed rectilinear frame of reference; (c) laying out a first alignment key having an axis aligned with an axis of the fixed first rectilinear frame of reference, the laid-out alignment key comprising a second set of graphical data; (d) transferring the rotated pattern and the first alignment key to a mask; and (e) placing the mask over a substrate comprising a hexagonal arrangement of CMOS cells having axes of symmetry respectively aligned with the axes of a second fixed rectilinear frame of reference, and a second alignment key having an axis aligned with an axis of the second fixed rectilinear frame of reference, the mask being placed so that the first alignment key is aligned with the second alignment key.

Another aspect of the invention is an alignment method comprising the following steps: (a) laying out a pattern representing a hexagonal arrangement of cMUT elements having axes of symmetry, the laid-out pattern comprising a first set of graphical data; (b) laying out a first alignment key having an axis, the laid-out alignment key comprising a second set of graphical data; (c) processing the second set of graphical data to rotate the first alignment key by a predetermined angle relative to the axes of symmetry, the predetermined angle being selected so that the axis of the first alignment key is aligned with one of the axes of symmetry of the hexagonal arrangement of hexagonal cMUT elements; (d) transferring the pattern and the rotated first alignment key to a mask; and (e) placing the mask over a substrate comprising a hexagonal arrangement of CMOS cells having orthogonal axes of symmetry respectively aligned with the axes of a second fixed rectilinear frame of reference, and a second alignment key having an axis aligned with an axis of the second fixed rectilinear frame of reference, the mask being placed so that the first alignment key is aligned with the second alignment key.

A further aspect of the invention is an integrated circuit comprising: a substrate comprising a hexagonal arrangement of CMOS cells; and a hexagonal arrangement of cMUT elements, wherein each micromachined element overlies a respective CMOS cell in one-to-one correspondence.

Yet another aspect of the invention is an integrated circuit comprising: a substrate comprising a hexagonal arrangement of CMOS cells; and a hexagonal arrangement of cMUT elements, wherein each cMUT element overlies a respective CMOS cell in one-to-one correspondence.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

Figure 1:
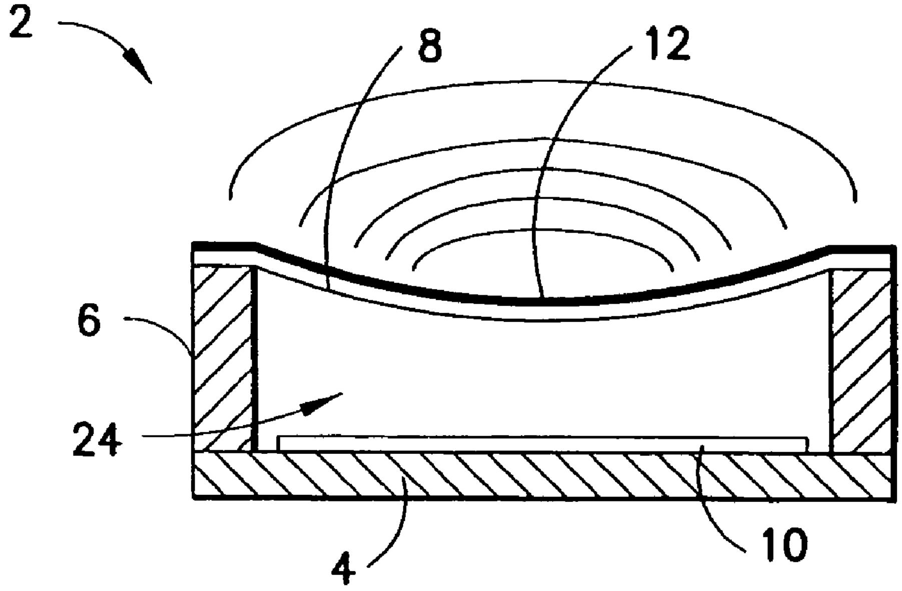
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 16 between the membrane 8 and the substrate 4 may be air- or gas-filled or wholly or partially evacuated. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the substrate.

Figure 2:
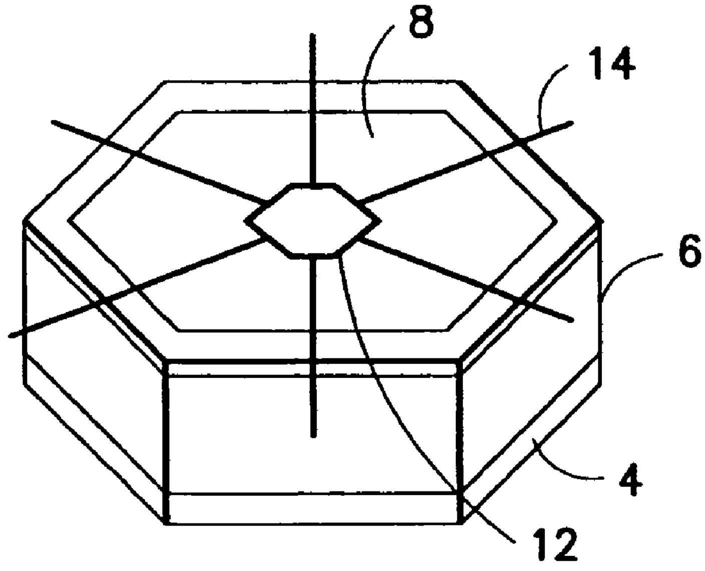
FIG. 2 is a drawing showing an isometric view of the cMUT cell shown in FIG. 1.

Due to the micron-size dimensions of a typical cMUT, numerous cMUT cells are typically fabricated in close proximity to form a single transducer element. The individual cells can have round, rectangular, hexagonal, or other peripheral shapes. A cMUT cell having a hexagonal shape is shown in FIG. 2. Hexagonal shapes provide dense packing of the cMUT cells of a transducer element. The cMUT cells can have different dimensions so that the transducer element will have composite characteristics of the different cell sizes, giving the transducer a broadband characteristic.

Figure 3:
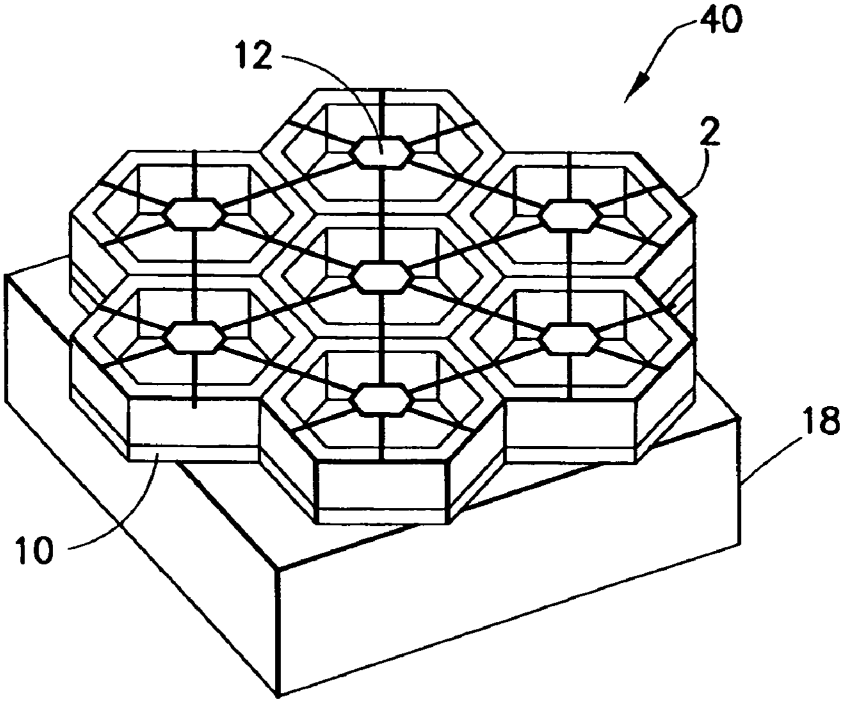
FIG. 3 is a drawing showing an isometric view of a hexagonal cMUT element built on top of a rectangular cell of integrated electronics in accordance with one embodiment of the invention. Neighboring elements and cells are not shown.

Each transducer element in a typical cMUT device is built with multiple cMUT cells. For the purpose of illustration, FIG. 3 shows a "daisy" transducer element made up of seven hexagonal cMUT cells 2: a central cell surrounded by a ring of six cells, each cell in the ring being contiguous with a respective side of the central cell and the adjoining cells in the ring. The top electrodes 12 of each cell 2 are hard-wired together. In the case of a hexagonal array, six conductors 14 (shown in both FIGS. 2 and 3) radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are electrically connected, forming a seven-times-larger capacitive transducer element 40.

Figure 4:
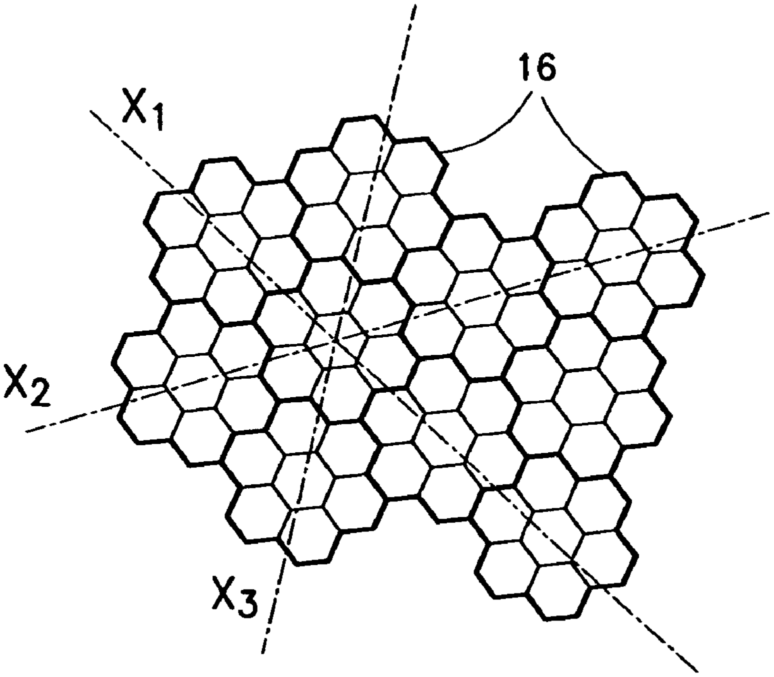
FIG. 4 is a drawing showing a top view of a hexagonal array of hexagonal cMUT elements with the three natural axes of symmetry superimposed.

In an ultrasound probe in which hexagonal cMUT elements 16 are distributed in a hexagonal pattern, there exist three natural axes of symmetry X1, X2, and X3 as shown in FIG. 4. These axes form a coordinate system that determines the array. The natural way to route signal and control lines in this coordinate system is along the axes of symmetry since they will then be straight uninterrupted lines as shown. In a CMOS device comprising rectangular CMOS cells arranged in a rectilinear grid, the natural axes of symmetry are orthogonal and do not align with the axes of symmetry of the hexagonal grid. Also the CMOS cells of the rectilinear grid cannot be matched with the cMUT elements of the hexagonal grid due to the inherent differences in geometry.

Figure 5:
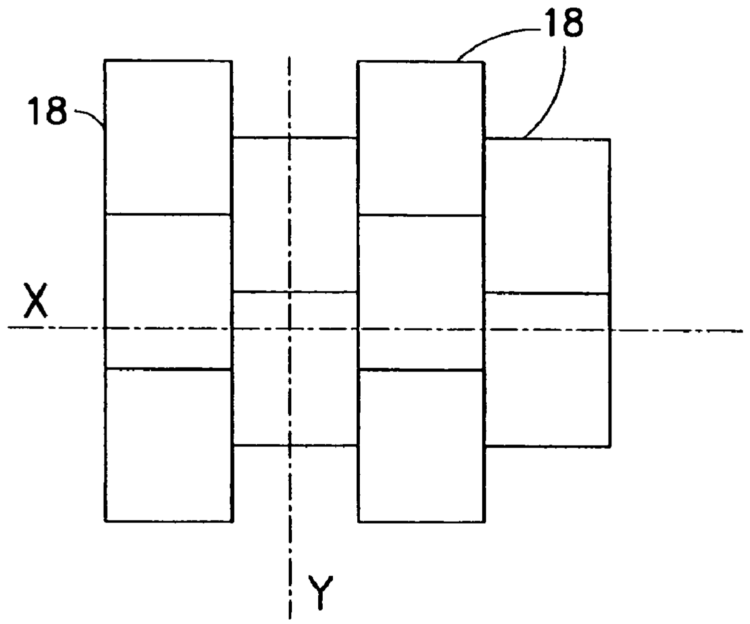
FIG. 5 is a drawing showing a top view of a hexagonal array of rectangular CMOS cells with the two orthogonal or rectilinear axes of symmetry superimposed.

In accordance with one embodiment of the invention, the foregoing problem is overcome by building the hexagonal grid of hexagonal cMUT elements on top of a hexagonal grid of rectangular CMOS cells. One example of a hexagonal grid of rectangular CMOS cells 18 having orthogonal axes X and Y is shown in FIG. 5. The hexagonal pattern is achieved by offsetting every other column by a distance equal to one-half of the cell dimension in the column direction. The lengths and widths of the rectangular CMOS cells are selected such that the distance between the centers of two rectangles along any diagonal will be equal to the distance between the centers of the two hexagonal cMUT elements overlying those CMOS cells.

The cMUT array is fabricated using optical lithography. Each layer in the micromachined structure requires its own mask. Each mask will have a coating with a geometric pattern for forming the structure seen in FIG. 4, i.e., a honeycomb or hexagonal pattern of hexagonal transducer elements, each transducer element being made up of a "daisy" pattern consisting of seven hexagonal cMUT cells. During layout of the mask, steps must be taken to ensure that the geometric pattern on each mask is properly aligned with the CMOS substrate about to be micromachined. All of the masks would be aligned to the same reference axes, and all of them would be rotated as necessary to align to the CMOS devices.

As disclosed herein, various methods can be used to ensure that the hexagonally distributed hexagonal cMUT elements are matched with the hexagonally distributed rectangular CMOS cells in the final fabricated structure. Two methods for ensuring proper alignment of the cMUT and CMOS layers are disclosed herein. However, the most appropriate method should be selected based on the available fabrication process.

In accordance with the methods disclosed herein, the CMOS cells are rectangular and offset by half of the cell height, as shown in FIG. 5. This offset is straightforward to accomplish. In this arrangement, lines can be easily routed along the rectangular grid axes.

Figure 6:
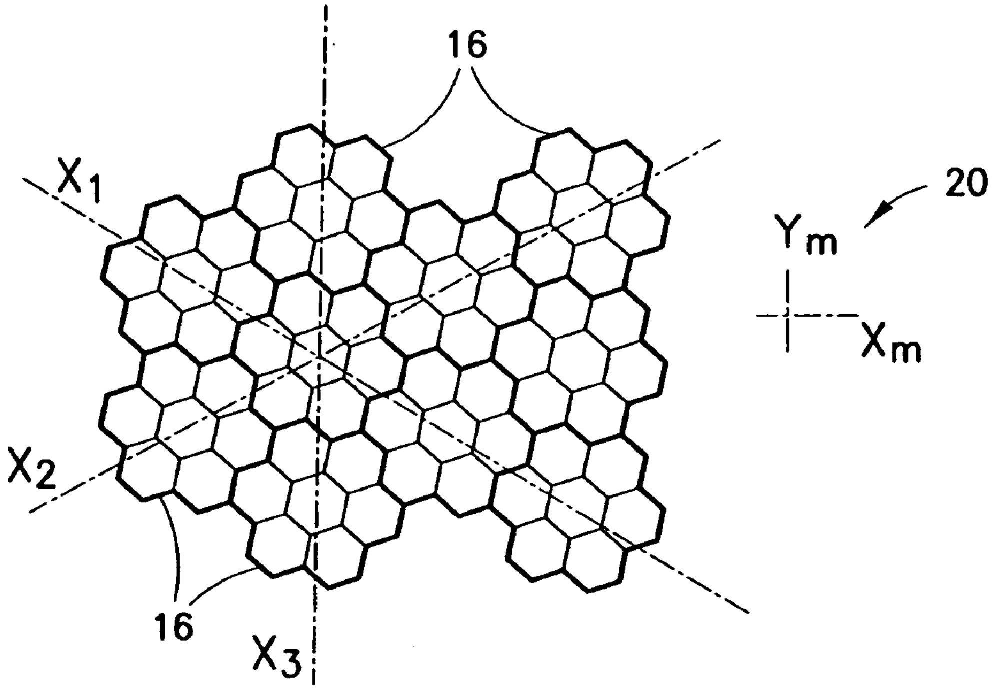
FIG. 6 is a drawing showing a layout for a hexagonal array of hexagonal cMUT elements that has been algorithmically rotated relative to an alignment key.

In accordance with a first method of the invention shown in FIG. 6, the hexagonal reference plane ($X_1$, $X_2$, $X_3$) is rotated relative to a rectilinear reference plane ($X_m$, $Y_m$) that is used within the cMUT layout tool. This rotation is accomplished algorithmically through manipulation of the vertices of the hexagonal cMUT elements during layout. More precisely, the rotation is accomplished by calculating what the new coordinates of each vertex would be once the geometric pattern is rotated a certain number of degrees away from the original axes. In addition, multiple alignment keys 20 (only one of which is shown in FIG. 6) are formed as part of the pattern on the mask. In the illustrated example, each alignment key 20 comprises two orthogonal intersecting straight lines that lie parallel to the respective axes $X_m$, $Y_m$ of the reference plane.

Figure 7:
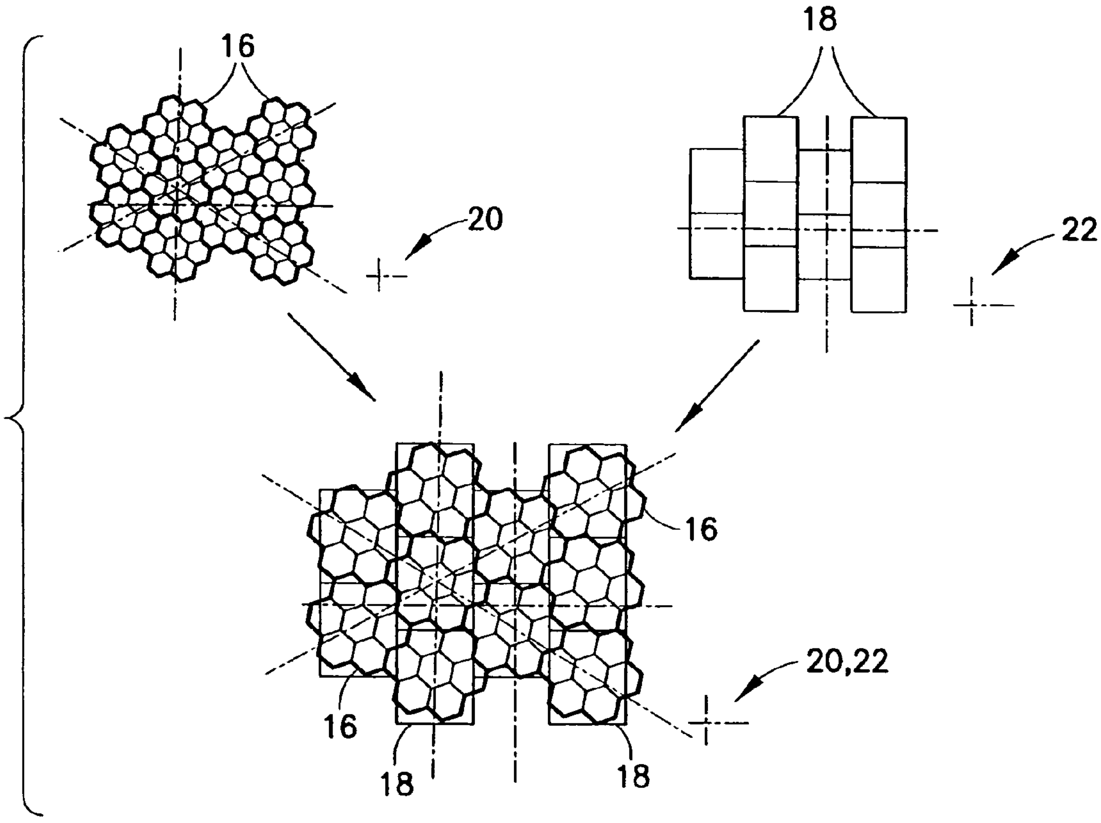
FIG. 7 is a drawing showing the alignment of a mask having a pattern for a hexagonal array of hexagonal cMUT elements with a hexagonal array of rectilinear CMOS cells.

Once the layout masks have been generated in this way, matching the hexagonal CMUT centers to the offset CMOS pattern shown in FIG. 5 is straightforward and is illustrated in FIG. 7. Multiple alignment keys 20 on the mask for patterning the cMUT layer must be respectively aligned with multiple alignment keys 22 formed on the CMOS substrate. Again, only one of each alignment key 20 and 22 is shown in FIG. 7. The lowermost portion of FIG. 7 depicts the cMUT mask overlying the CMOS substrate, with the hexagonal patterns on the mask correctly aligned with the rectangular CMOS cells in the substrate. In this positional relationship, the alignment keys 20 will be superimposed on top of the respective alignment keys 22. For the particular example shown in FIG. 7, the overlapped alignment key 22 is not visible because it lies underneath the alignment key 20. However, a person skilled in the art will appreciate that the alignment keys are typically designed so that the key 20 on the mask will fit inside the key 22 on the wafer, allowing both keys to be visible during alignment.

Figure 8:
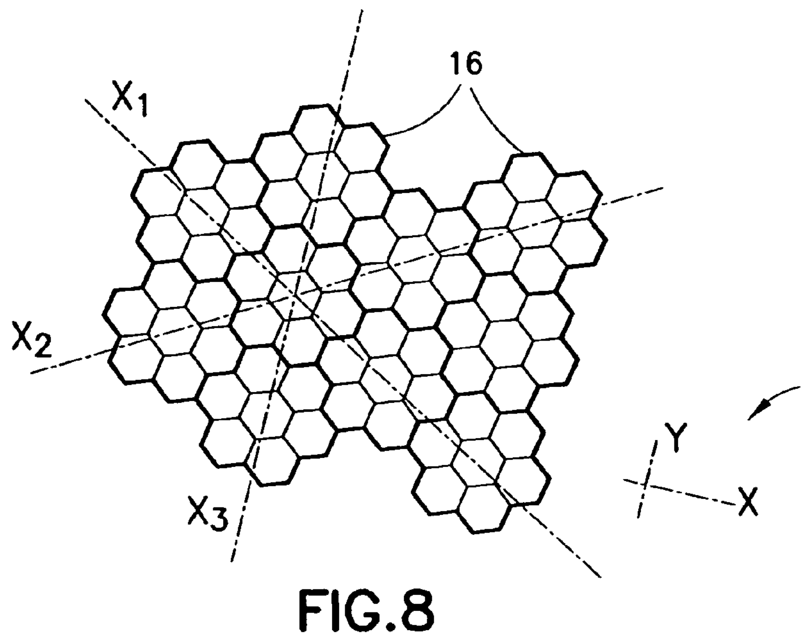
FIG. 8 is a drawing showing a layout for a hexagonal array of hexagonal cMUT elements and for an alignment key that has been algorithmically rotated relative to the axes of symmetry of the hexagonal array.

In accordance with a second method of the invention shown in FIG. 8, the hexagonal reference plane ($X_1$, $X_2$, $X_3$) is designed as is most convenient in the cMUT layout tool. Within this tool, a plurality of mask alignment keys 20 (only one of which is seen in FIG. 8) are added which are rotated by the matching angle. This means that the Y axis of the alignment key 20 is parallel to the $X_3$ axis in the cMUT plane. During fabrication of the cMUTs, the masks are rotated and aligned relative to similar alignment keys located on the CMOS wafer. In this way, matching of the hexagonal cMUT centers to the offset CMOS pattern shown in FIG. 5 is straightforward. The end result will again be the structure depicted in FIG. 7.

Thus, in accordance with the first disclosed method, the cMUT frame of reference is rotated during mask layout by designing the cMUT hexagonal axes to be rotated with respect to a rectilinear reference grid in the cMUT plane, while in accordance with the second disclosed method, the cMUT frame of reference is rotated during lithography by rotating the mask exposure relative to the CMOS plane of reference using fiducial keys located on the CMOS device. In both methods, the CMOS substrate incorporates alternate half-step offsetting of CMOS cell columns to line up with the rotated cMUT cells.

The advantages provided by the foregoing methods of alignment are manifold: 1) the need for lines which are not rectilinear in the CMOS layer is eliminated, thereby simplifying mask layout in the CMOS cells; 2) these methods allow for rectangular CMOS cells that are uniformly spaced, which simplifies mask layout for lithographic construction of the CMOS cells; 3) these methods allow the use of rectilinear layout rules in CMOS lithography, which is the standard (non-rectilinear layout rules are often discouraged by semiconductor manufacturers); 4) the potential for yield losses due to mispatterned lines that are not rectilinear is eliminated; and 5) these methods allow for precise matching of rectangular CMOS cells with hexagonal cMUT cells.

The disclosed alignment methods are not limited to use with cMUTs, but rather can also be applied when fabricating an array of hexagonal micromachined devices on top of a corresponding array of rectangular electronics cells.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. An alignment method comprising the following steps:

laying out a pattern representing a hexagonal arrangement of cMUT elements having axes of symmetry, said laid-out pattern comprising a first set of graphical data;

processing said first set of graphical data to rotate said pattern by a predetermined angle relative to a fixed rectilinear frame of reference having two mutually orthogonal axes, said predetermined angle being selected so that an axis of symmetry of said hexagonal arrangement of hexagonal cMUT elements is aligned with an axis of a first fixed rectilinear frame of reference;

laying out a first alignment key having an axis aligned with an axis of said fixed first rectilinear frame of reference, said laid-out alignment key comprising a second set of graphical data;

transferring said rotated pattern and said first alignment key to a mask; and placing said mask over a substrate comprising a hexagonal arrangement of CMOS cells having axes of symmetry respectively aligned with the axes of a second fixed rectilinear frame of reference, and a second alignment key having an axis aligned with an axis of said second fixed rectilinear frame of reference, said mask being placed so that said first alignment key is aligned with said second alignment key.

2. The method as recited in claim 1, wherein each of said cMUT elements is hexagonal and each of said CMOS cells is rectangular.

3. An alignment method comprising the following steps:

laying out a pattern representing a hexagonal arrangement of cMUT elements having axes of symmetry, said laid-out pattern comprising a first set of graphical data;

laying out a first alignment key having an axis, said laid-out alignment key comprising a second set of graphical data;

processing said second set of graphical data to rotate said first alignment key by a predetermined angle relative to said axes of symmetry, said predetermined angle being selected so that said axis of said first alignment key is aligned with one of said axes of symmetry of said hexagonal arrangement of hexagonal cMUT elements;

transferring said pattern and said rotated first alignment key to a mask; and placing said mask over a substrate comprising a hexagonal arrangement of CMOS cells having orthogonal axes of symmetry respectively aligned with the axes of a second fixed rectilinear frame of reference, and a second alignment key having an axis aligned with an axis of said second fixed rectilinear frame of reference, said mask being placed so that said first alignment key is aligned with said second alignment key.

4. The method as recited in claim 3, wherein each of said cMUT elements is hexagonal and each of said CMOS cells is rectangular.

* * * * *

UNITED STATES PATENT AND TRADEMARK OFFICE

CERTIFICATE OF CORRECTION

PATENT NO. : 7,052,464 B2 | Page 1 of 1
APPLICATION NO. : 10/751290
DATED : May 30, 2006
INVENTOR(S) : Robert G. Wodnicki It is certified that error appears in the above-identified patent and that said Letters Patent is hereby corrected as shown below:

Column 1, line 10, replace “DAND17-02-1-0181” with --DAMD17-02-10181--.

Signed and Sealed this

Eighteenth Day of August, 2009

David J. Kappos

*Director of the United States Patent and Trademark Office*